United States Patent [19]

Katz et al.

[11] Patent Number: 4,944,313

[45] Date of Patent: Jul. 31, 1990

[54] SINGLE-USE ANNULAR MOUTHPIECE

[75] Inventors: Seymour Katz, Glen Cove, N.Y.; Marna L. Schirmer, Norwalk, Conn.

[73] Assignee: E-Z-EM, Inc., Westbury, N.Y.

[21] Appl. No.: 403,693

[22] Filed: Sep. 6, 1989

[51] Int. Cl.[5] .............................................. A61B 1/00
[52] U.S. Cl. .................................... 128/859; 128/861; 128/207.14
[58] Field of Search ................ 128/847, 848, 857–862, 128/200.26, 207.14, 207.17

[56] References Cited

U.S. PATENT DOCUMENTS

| | | | |
|---|---|---|---|
| 1,674,336 | 6/1928 | King | 128/848 |
| 2,589,504 | 3/1952 | Miller | 128/857 |
| 3,060,935 | 10/1962 | Riddell | 128/861 |
| 3,411,501 | 11/1968 | Greenberg | 128/862 |
| 3,682,164 | 8/1972 | Miller | 128/861 |
| 3,692,025 | 9/1972 | Greenberg | 128/861 |
| 3,864,832 | 2/1975 | Carlson | 128/862 |
| 4,173,505 | 11/1979 | Jacobs | 128/861 |
| 4,502,478 | 3/1985 | Lifton | 128/862 |
| 4,640,273 | 2/1987 | Green | 128/861 |
| 4,765,324 | 8/1988 | Lake, Jr. | 128/861 |

Primary Examiner—Robert A. Hafer
Assistant Examiner—Michael Brown
Attorney, Agent, or Firm—McAulay Fisher Nissen & Goldberg

[57] ABSTRACT

A single-use annular mouthpiece for use with a diagnostic instrument such as an endoscope is provided. The mouthpiece protects the endoscope from damage and enhances patient comfort while giving a visible indication of any prior use. The mouthpiece includes a first relatively rigid portion having an annular main body shaped and dimensioned to be held in a patient's mouth and to provide clearance for an instrument through its central opening. The rigid portion includes an annular lip extending radially from the main body at one end and an annular flange extending radially from the main body at another end. The flange is shaped and dimensioned to overlie a patient's lips. The mouthpiece includes a second deformable compressible annular portion mounted around the annular main body of the first portion. The second portion is permanently deformable when subject to a patient'bite. The second portion is sized and shaped to substantially encircle the main body portion and to fit between the lip and the flange. The outer periphery of the lip extends no further than the outer surface of the second compressible annular portion.

23 Claims, 1 Drawing Sheet

SINGLE-USE ANNULAR MOUTHPIECE

BACKGROUND OF THE INVENTION

The present invention is directed to a mouthpiece for use with a diagnostic instrument such as an endoscope. Endoscopy and other medical procedures require that an expensive instrument which includes relatively fragile components be inserted, via a patient's mouth, into the patient's body cavity.

Endoscopes and other types of medical instruments include fragile internal mechanisms which are contained in a tube. When inserting an instrument such as an endoscope into a patient's mouth, it is important to prevent damage to the endoscope and the patient. When tubes are inserted, patients will tend both reflexively and deliberately to bite on the tube. Such biting may damage the internal components of the instrument.

In performing procedures such as endoscopy, it is desirable to make the procedure as comfortable as possible for the patient. It is also important to insure that any device which contacts the patient is free from cross contamination from infectious diseases. One way of providing for freedom from cross contamination is to employ single-use devices. However, for practical reasons, single-use devices must be relatively inexpensive. To insure that single-use devices are not reused, it is helpful to have an easily ascertained indication of any prior use of the device.

It is known in the art to insert an endoscope or other device through a mouth guard or a mouthpiece which has previously been inserted in the patient's mouth. The mouthpiece insures that the patient's jaws are kept open a sufficient distance to permit insertion of the instrument and further protect the instrument from damage. Many of these prior art mouthpieces have been made of a rigid material since their primary purpose has been to protect the instrument. However, the rigidity of the mouthpiece results in discomfort to the patient and in possible injury to the patient from biting down on the rigid material. Further, as with any object inserted into the mouth, the mouthpieces tend to cause a gagging response in the patient if the mouthpiece is too large.

One example of a mouth guard designed to both protect a patient as well as the diagnostic instrument is disclosed in United States Letters Pat. No. 4,640,273 issued on Feb. 3, 1987 to Franklin R. Greene et al. The '273 patent discloses a mouth guard having a rigid core to protect the endoscope and a relatively flexible coat to cushion the patient's bite and thus protect the patient. The '273 mouth guard in use is neither rigid enough to adequately protect the instrument or compressible enough to provide adequate patient comfort. Further, the mouth guard extends too far into the patient's mouth to sufficiently avoid a gagging response.

It is an object of the present invention to provide a mouthpiece which protects both the instrumentation passed therethrough and the patient.

Another object of the present invention is to provide such a mouthpiece which is relatively inexpensive to manufacture.

Still a further object of the present invention is to provide such a simple mouthpiece which can be easily used and which is safe in use.

Still a further object of the present invention is to provide such a mouthpiece which is relatively comfortable and which doesn't cause gagging.

Another object of the present invention is to provide such a mouthpiece which will indicate if the mouthpiece has been used previously.

BRIEF DESCRIPTION

In brief the present invention relates to a annular mouthpiece for use with a medical instrument such as an endoscope. The mouthpiece is intended for single-use. The mouthpiece includes a relatively rigid portion with an annular body segment, an annular lip extending radially out from the annular body segment at one end thereof and, an annular flange connected to the annular body segment at the other end thereof. The annular body segment has a central opening to provide clearance for an instrument. The annular body segment and the lip are shaped and dimensioned to be held in a patient's mouth. The flange is shaped and dimensioned to overlie a patient's lips. The mouthpiece includes a deformable, compressible annular portion mounted around the annular body segment of the rigid portion. The compressible portion is permanently deformable when subject to a patient's bite. The compressible portion is sized and shaped to substantially encircle the annular body segment and to sit securely between the annular lip and the flange. The outer periphery of the lip extends no further than the outer surface of the compressible annular portion.

DESCRIPTION OF THE PREFERRED EMBODIMENT

Figure 1:
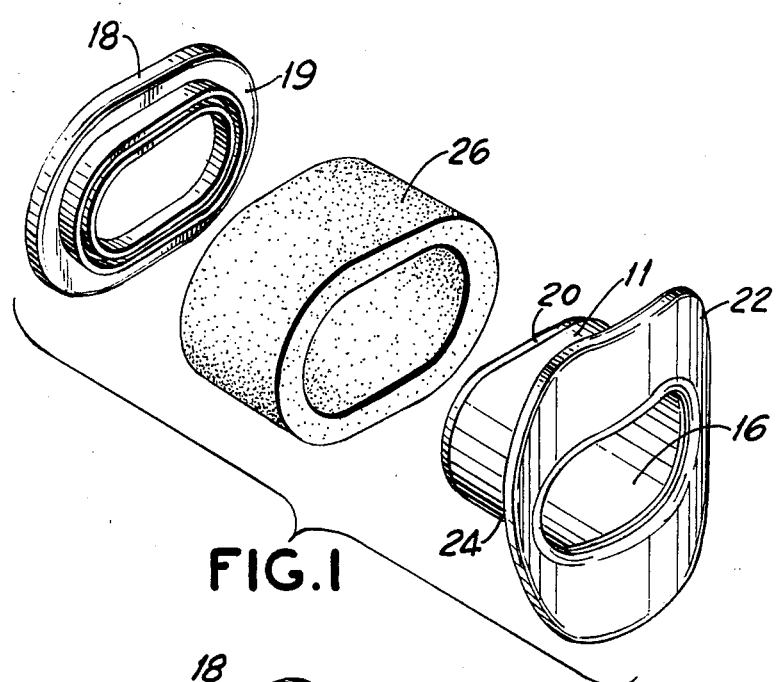
FIG. 1 is an exploded view of one embodiment of the single-use annular mouthpiece of the present invention.
Figure 2:
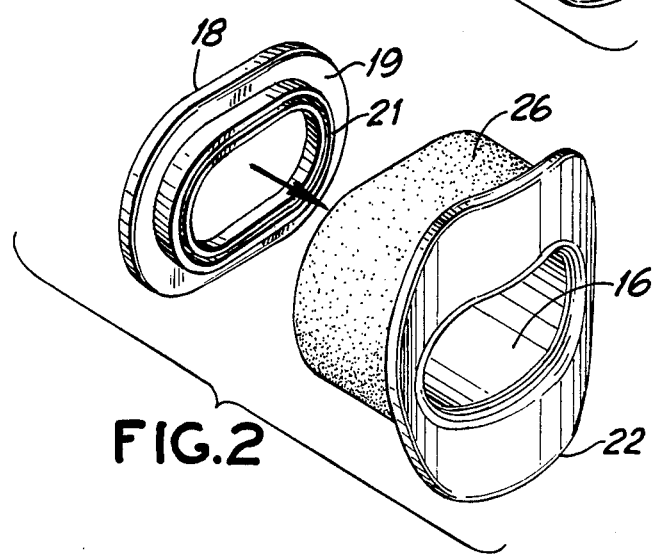
FIG. 2 is a partially exploded view of the FIG. 1 mouthpiece showing the compressible annular piece mounted on the annular body of the rigid piece before the annular lip is connected thereto.
Figure 4:
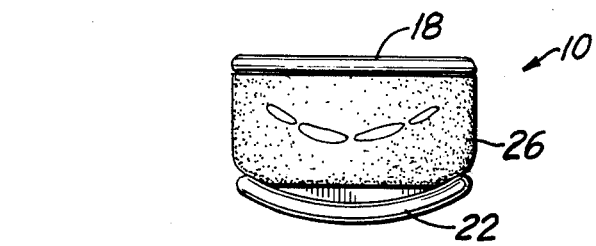
FIG. 4 is a top plan view of the FIG. 3 mouthpiece showing the mouthpiece after it has been used by a patient and the compressible portion has been deformed by the patient's bite.
Figure 3:
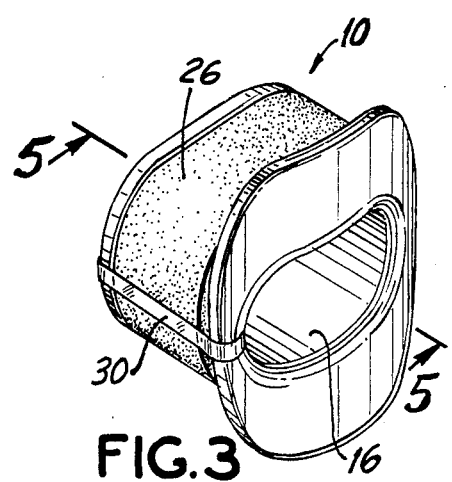
FIG. 3 is a perspective view of an embodiment of the annular mouthpiece of the present invention showing the polypropylene tape wrapped about the compressible annular piece and the rigid portion.
Figure 5:
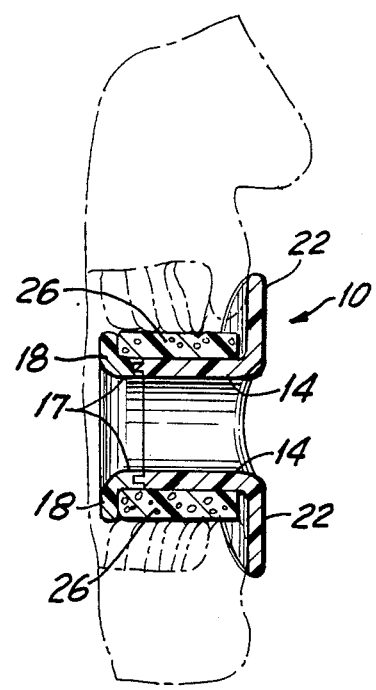
FIG. 5 is sectional view of the FIG. 3 mouthpiece taken generally along line 5—5 of FIG. 3 and showing the mouthpiece held in a patient's mouth.

Referring to the drawings, the reference numeral 10 generally denotes the single-use mouthpiece of the present invention. Mouthpiece 10 is shaped and dimensioned to fit, with a reasonable degree of comfort, in an adult patient's mouth and is also shaped and dimensioned to accommodate most endoscopes and other related medical instruments.

Mouthpiece 10 has a rigid portion which is sufficiently rigid to protect the endoscope or other medical instrument intended for use with the mouthpiece 10. In a preferred embodiment of the present invention the rigid portion is formed of injection molded polypropylene. The rigid portion is comprised of an annular body segment 14, an annular lip 18, and an annular flange 22.

Annular body segment 14 is shaped and dimensioned to be held in a patient's mouth and is formed with a central opening 16 through which an endoscope may be inserted.

Annular lip 18 extends radially out from annular body segment 14 at a first end 20 thereof. Annular flange 22 extends radially out from annular body segment 14 at a second end 24 thereof. Flange 22 is shaped and dimensioned to overly a patient's lip.

The dimensions of annular lip 18 provide for a reasonably comfortable fit in the mouth of an average adult patient. In a preferred embodiment of the present invention, the major axis of the outer rim of annular lip 18 is about 1.56 inches and the minor axis of the outer rim is about 1.225 inches.

The major axis of central opening 16 is about 1.19 inches and its minor axis is about 0.625 inches. The major axis of the outer rim of annular flange is about 1.955 inches and the minor axis of its outer rim is about 1.56 inches.

A compressible, deformable, annular piece 26 is mounted around annular body segment 14 of the rigid portion. Annular piece 26 is permanently deformable when subject to a patient's bite. Due to its deformable nature the annular piece provides a readily visible indication of any prior use of the mouthpiece to thus prevent any inadvertent reuse thereof. Annular piece 26 is sized and shaped to substantially encircle the annular body segment 14 and to fit securely between lip 18 and flange 22.

In a preferred embodiment, annular piece 26 is made of a die-cut, closed cell, foamed polyolefin. Annular piece 26 has a thickness of about 0.265 inches. The polyolefin can be elongated 180% before breakage which allows it to stretch around and hold securely against annular body segment 14. The polyolefin has a compression set of 13% of its original thickness to allow it to deform when subject to a patient's bite. One example of a polyolefin useable to form annular piece 26 is Minicel L200 available from Voltek Division of Sekisui America Corp. of Lawrence, Massachusetts. The inner periphery of annular piece 26 has a minor axis of about 0.625 inches and a major axis of about 1.125 inches. The dimensions of annular piece 26 and the material from which it is made, in combination with the dimensions of the annular body segment 14 provide for a stretch fit of the annular piece 26 on annular segment 14.

Lip 18 is sized and dimensioned to provide a ledge 19 having a depth of about 0.18 inches. Annular piece 26 abuts against ledge 19 to prevent the annular piece 26 from slipping from the annular body segment 14. To help insure patient comfort, the outer periphery of lip 18 is as small as possible, and preferably the outer periphery of lip 18 extends no further than the outer surface of annular piece 26.

Although the annular piece 26 is held securely in place by lip 18, to further insure that annular piece 26 does not slip from annular body segment 14, polypropylene tape 30 is wrapped around both annular piece 26 and the rigid portion of the mouthpiece.

The axial length of mouthpiece 10 is about 1.065 deep. The portion of mouthpiece 10 which is intended to be held in the patient's mouth has an axial length of about 0.80 inches deep. This depth is sufficiently small to minimize gagging.

Annular body segment 14, proximate to end 20 thereof, is formed with peripheral tongue 17. Lip 18 is formed with a peripheral grove 21 shaped and dimensioned to receive tongue 17.

Mouthpiece 10 is manufactured in the following manner. The rigid portion is injection molded in two segments. The annular body segment 14 and the annular flange 22 comprise one segment and the annular lip 18 comprise a second segment. The compressible annular piece 26 is die-cut from a cross-linked polyolefin foam. Annular piece 26 is stretched and mounted on annular body segment 14. The annular lip 18 is then ultrasonically welded t the first segment of the rigid portion with tongue 17 received in grove 21. The annual piece 26 is thus captured securely on the annular body segment 14 with one end abutting against ledge 19. To provide extra security, polypropylene tape 30 is then wrapped around annular piece 26 and the rigid portion of the mouthpiece to secure the annular piece 26 in position.

What is claimed:

1. A single-use annular mouthpiece comprising:
   a relatively rigid portion including an annular main body shaped and dimensioned to be held in a patient's mouth and to provide clearance for tubing through its central opening,
   an annular lip extending radially out from said main body at one end thereof,
   an annular flange extending radially out from said main body at the other end thereof, said flange being shaped and dimensioned to overlie a patient's lips; and
   a compressible annular portion severable from and mounted around to overlie said annular main body of said rigid portion,
   said portion being sized and shaped to encircle said main body portion and to fit between said lip and said flange,
   the outer periphery of said lip extending radially out no further than the outer surface of said compressible annular portion,
   whereby said mouthpiece is usable in medial and surgical procedures which require both protection for tubing used with the mouthpiece and protection for the patient undergoing the procedure.

2. The mouthpiece of claim 1 wherein said compressible annular portion is deformable.

3. The mouthpiece of claim 2 wherein said deformable compressible annular portion is permanently deformed when subjected to a patient's bite.

4. The mouthpiece of claim 3 wherein:
   said deformable, compressible annular portion is formed of a foamed polyolefin.

5. The mouthpiece of claim 4 wherein said foamed polyolefin is closed-celled having an elongation of 180 percent before breakage and a compression set of about 13% of original thickness.

6. The mouthpiece of claim 3 and further comprising a band of polypropylene tape wrapped around said second portion and said rigid portion.

7. The mouthpiece of claim 3 wherein said annular flange has a major axis of about 1.95 inches and a minor axis of about 1.56 inches.

8. The mouthpiece of claim 3 wherein said annular lip has a major axis of about 1.56 inches and a minor axis of about 1.22 inches.

9. The mouthpiece of claim 3 wherein said deformable portion has a thickness of about 0.27 inches.

10. The mouthpiece of claim 3 wherein the portion of said mouthpiece held in a patient's mouth has an axial length of about 0.80 inches.

11. The mouthpiece of claim 3 wherein said deformable portion has a major axis of about 1.12 inches and a minor axis of about 0.63 inches.

12. The mouthpiece of claim 3 wherein said rigid portion is formed with a central opening having a major axis of about 1.19 inches and a minor axis of about 0.625 inches.

13. The mouthpiece of claim 12 wherein said annular flange has a major axis of about 1.95 inches and a minor axis of about 1.56 inches, said annular lip has a major axis of about 1.56 inches and a minor axis of about 1.22 inches, said deformable portion has a major axis of about 1.12 inches, a minor axis of about 0.63 inches and thickness of about 0.27 inches, and said portion of said mouthpiece held in a patient's mouth has an axial length of about 0.80 inches.

14. The mouthpiece of claim 13 and further comprising a band of polypropylene tape wrapped around said deformable portion and said rigid portion.

15. The mouthpiece of claim 3 wherein said annular lip provides a ledge against which said deformable portion abuts when mounted on said annular main body.

16. The mouthpiece of claim 15 wherein said ledge has a depth of about 0.18 inches.

17. The mouthpiece of claim 3 wherein said annular body segment has a peripheral tongue and said lip has a peripheral groove, said groove shaped and dimensioned to receive said tongue.

18. The mouthpiece of claim 3 wherein said rigid portion is formed of polypropylene.

19. A method for manufacturing a single-use mouthpiece comprising the steps of:
   molding a relatively rigid first piece which includes an annular main body shaped and dimensioned to be held in a patient's mouth and to provide clearance for tubing through a central opening, and an annular flange extending radially out from said main body at one end thereof, said flange being shaped and dimensioned to overlie a patient's lips;
   molding a relatively rigid annular lip;
   die-cutting a compressible annular portion which is shaped and dimensioned to encircle said main body portion and to fit between said annular lip and said annular flange when said annular lip is connected to said main body portion;
   mounting said compressible portion on said main body portion so that it overlies said main body portion; and
   then welding said annular lip to said first relatively rigid portion to securely capture said deformable portion between said lip and said flange.

20. The method of claim 19 wherein said first and second pieces are injection molded.

21. The method of claim 19 and further comprising the step of wrapping polypropylene tape around said second portion and said rigid portion.

22. The method of claim 19 wherein said main body is formed with a groove and said lip is formed with a tongue, said tongue shaped dimensioned to be received within said groove prior to the welding of said first and second pieces.

23. The method of claim 19 wherein said welding is ultrasonic.

* * * * *